(12) United States Patent
Beyerer et al.

(10) Patent No.: US 6,965,120 B1
(45) Date of Patent: Nov. 15, 2005

(54) METHOD AND APPARATUS FOR QUALITY CONTROL IN THE MANUFACTURE OF FOUNDRY CORES OR CORE PACKETS

(75) Inventors: Jürgen Beyerer, Dielheim (DE); Mohammed Ali Seiraffi, Schwetzingen (DE)

(73) Assignee: Hottinger Maschinenbau GmbH, Mannheim (DE)

( * ) Notice: Subject to any disclaimer, the term of this patent is extended or adjusted under 35 U.S.C. 154(b) by 0 days.

(21) Appl. No.: 09/868,716

(22) PCT Filed: Dec. 21, 1999

(86) PCT No.: PCT/DE99/04070

§ 371 (c)(1),
(2), (4) Date: Jun. 20, 2001

(87) PCT Pub. No.: WO00/37926

PCT Pub. Date: Jun. 27, 2000

(30) Foreign Application Priority Data

Dec. 21, 1998 (DE) ................................. 198 60 309

(51) Int. Cl.⁷ ........................................... G01N 21/88
(52) U.S. Cl. ........................... 250/559.45; 250/559.39; 382/141
(58) Field of Search ...................... 250/559.39, 559.42, 250/559.12, 559.45, 224, 208.1; 356/239.4, 356/239.7, 239.8, 240.1, 237.3, 237.2, 237.4, 356/237.5, 237.6, 390, 392, 394; 382/141, 382/149; 209/576, 577; 348/125–130; 702/153

(56) References Cited

U.S. PATENT DOCUMENTS

| | | | | |
|---|---|---|---|---|
| 4,736,437 A | * | 4/1988 | Sacks et al. | 382/216 |
| 4,782,238 A | * | 11/1988 | Radl et al. | 250/559.36 |
| 4,873,651 A | * | 10/1989 | Raviv | 700/259 |
| 4,882,498 A | | 11/1989 | Cochran et al. | 250/559.04 |
| 4,969,037 A | | 11/1990 | Poleschinski et al. | 348/370 |
| 5,064,291 A | * | 11/1991 | Reiser | 348/131 |
| 5,369,492 A | | 11/1994 | Sugawara | 356/394 |
| 5,440,391 A | * | 8/1995 | Smeyers et al. | 356/237.1 |
| 5,519,496 A | | 5/1996 | Borgert et al. | 356/394 |
| 5,757,506 A | * | 5/1998 | Tabatabaei | 356/400 |

(Continued)

FOREIGN PATENT DOCUMENTS

| | | |
|---|---|---|
| DE | 31 48 461 C1 | 4/1983 |
| DE | 44 34 798 A1 | 5/1995 |
| DE | 195 34 984 C1 | 8/1996 |

(Continued)

*Primary Examiner*—David Porta
*Assistant Examiner*—Stephen Yam
(74) *Attorney, Agent, or Firm*—Alston & Bird LLP

(57) ABSTRACT

A method and an apparatus for object recognition, in particular defect detection on workpieces, such as shot cores (1) or core packets, wherein the object is illuminated by a light source (4) and recorded and detected by means of a camera (3), and wherein the data obtained from the recording are processed or, if need be, stored by means of a computer. The object is illuminated by a least two light sources (4) from different directions or angles, and the camera (3) records the object and the shadows resulting from the illumination.

14 Claims, 2 Drawing Sheets

U.S. PATENT DOCUMENTS

| | | | |
|---|---|---|---|
| 5,956,134 A * | 9/1999 | Roy et al. | 348/126 |
| 5,963,328 A * | 10/1999 | Yoshida et al. | 356/237.2 |
| 5,996,681 A | 12/1999 | Pohlandt | 164/456 |
| 6,169,282 B1 * | 1/2001 | Maeda et al. | 250/310 |
| 6,177,682 B1 * | 1/2001 | Bartulovic et al. | 250/559.44 |
| 6,529,625 B2 * | 3/2003 | Sentoku et al. | 382/151 |

FOREIGN PATENT DOCUMENTS

| | | |
|---|---|---|
| EP | 0 356 680 A1 | 3/1990 |
| EP | 0 662 609 A2 | 7/1995 |
| EP | 0 840 107 A2 | 5/1998 |
| JP | 10288517 | 10/1998 |

\* cited by examiner

METHOD AND APPARATUS FOR QUALITY CONTROL IN THE MANUFACTURE OF FOUNDRY CORES OR CORE PACKETS

BACKGROUND OF THE INVENTION

The invention relates to a method of recognizing objects, in particular detecting defects on workpieces, preferably on shot cores or core packets, wherein the object is illuminated by a light source and recorded or detected by means of a camera, and wherein the data obtained from the recording are processed and, if need be, stored by means of a computer.

Furthermore, the invention relates to an apparatus for recognizing objects, in particular for applying the method according to the invention.

In generic terms, the invention quite generally relates to a method for recognizing objects or detecting defects on workpieces. Quite particularly, this method is suited for detecting defects on shot cores or core packets. To this extent, the invention also relates, among other things, to the field of foundry practice.

For casting mold parts of any kind, foundry cores or molds are made in most cases in separate pieces, combined, and joined to a casting mold or a core packet. These core packets are then filled with a molten metal for making, for example, a metallic work piece. In the series production, the core packets to be filled with the molten metal pass, one after the other, through a production line.

In this connection, it is particularly important that the workpieces cast in the core packets require an extremely long cooling phase, which often extends over several hours. Only after this cooling phase, is it possible to inspect the cast workpiece or part. Consequently, it is possible to find out only several hours after the casting, and thus likewise only several hours after the core shooting, whether the part cast in the core packet is indeed free of defects.

Should a defective core have been used, it would be possible to detect resultant rejects only hours after making the core. Should it in turn be a systematic, for example, a recurrent defect on the core because of a defect on the tool, rejects would be produced for hours before the defect is identified on the cast part. As previously mentioned, the defective cores responsible for these rejects could originate not only from defects in the tool of the core shooting machine, but also from direct damage to the cores during their handling, transportation, or assembly. In any event, it is not justifiable to be able to detect defects and thus rejects only after completing the casting operation, or during the inspection of the cast parts that have already cooled.

Moreover, damage to mold parts and/or tools may occur not only in the immediate vicinity of the shooting device, but rather also in any handling of the mold part and/or tool, during transportation, in the machining of the mold parts, during the cleaning of the tools, and in particular also during the assembly of the mold parts to whatever shape of a mold packet.

Core and shell shooting machines of the above-described kind have been known from practice for many decades. For example, one may refer to DE 31 48 461 C1, which discloses a core and shell shooting machine as made by Applicant.

Likewise, DE 44 34 798 A1 discloses a core and shell shooting machine, which is provided with at least one visual inspection of the tool. Last but not least, the visual control as addressed in DE 44 34 798 A1 is not practicable, inasmuch as it is not possible to observe the tool constantly within the scope of a fully automatic production. For a visual inspection, a skilled worker would have to observe the tool constantly, i.e., after each shooting operation. Even if one performed such a visual observation or inspection, the fate of an ejected core that is to be transported, machined, or assembled to a packet, would be left fully open, inasmuch as defects or damage may also occur during the handling or machining of the cores, during the transfer of the cores, or even during the assembly of the cores to packets.

DE 195 34 984 C1 already discloses a generic method, wherein the mold part or the core is measured, among other things, by a noncontacting technique even after its removal from the core shooting machine. This occurs in an advantageous manner by means of a camera, which requires in this instance an adequate illumination. Concealed regions or undercuts can be inspected by this kind of method only, when either a plurality of cameras are used for the image recording, and thus likewise for detecting defects, or when a camera is moved relative to the location of the object or core being examined. Both variants require a considerable expenditure for apparatus, and therefore are problematic for cost reasons alone. Furthermore, the arrangement of a plurality of cameras interferes with the direct surroundings of the particular core, and thus with the manipulators being used in this region.

It is therefore an object of the present invention to improve and further develop a method of the generic kind as well as a corresponding apparatus for object recognition, in particular for detecting defects on workpieces, preferably on shot cores or core packets in such a manner that they enable an adequately satisfactory object recognition and defect detection with the least possible expenditure for apparatus or construction.

SUMMARY OF THE INVENTION

Accordingly, a generic method of the above-described kind is characterized in that the object is illuminated by at least two light sources from different directions or angles, and that the camera records the object and the shadows resulting from the illumination, for example, on the object or a base. In this process, the different light sources may be switched on one after the other with respect to time (time division multiplex), or—in the case of a continuous operation of all or individual light sources—they may be of a different color (color division multiplex, wavelength division multiplex). Furthermore, polarization multiplexes are possible with a correspondingly polarized light. The shadows may form on the object itself, on a base, a wall, or a screen, or the like by a corresponding arrangement of the light sources and projections resulting therefrom.

In accordance with the invention, it has been recognized that it will also be possible to detect with a single camera irregularly shaped objects, for example, objects with undercuts, niches, cutouts, etc., as regards possible defects, when a very special illumination is provided. Deviating from previously known methods of the kind under discussion, one uses for illuminating the object being examined at least two light sources adapted for sequential and color differentiation. The two light sources illuminate the object from different directions or angles—one after the other or in groups—namely according to the geometry of the particular object. According to the arrangement of the light source relative to the particular object, a shadow of a part of the object is projected onto the base or onto other parts of the object, so that the object can be "extended" or "spread" by means of a shadow cast. In other words, the skillful arrangement of the light sources permits projecting regions that are otherwise not recognizable with a single camera, from their "concealed" position, and recording same as quasi additional image information supplementing the contours of the object. Thus, it is possible to perform a very satisfactory examination of critical regions, which are especially susceptible to possible defects, and to even enlarge them by a suitable projection for purposes of such an—optical—examination, thereby promoting in turn a satisfactory detection.

In a quite particularly advantageous manner, the illumination or the light sources are switchable, for example by electronic means or by means of mechanical shutters. It is likewise possible to use for this purpose tubular fluorescent lamps without electrodes.

The illumination selected in accordance with the invention is insensitive to vibrations. More specifically, vibrations will barely affect the illumination, since the object is illuminated by a very wide light cone. However, the camera records quasi point by point, and insofar it can over and above be miniaturized.

In accordance with the invention, 3-D image data are used for detecting defects, namely on the basis of the illumination of the object concretely claimed herein.

In an advantageous manner, the object is illuminated from different directions or angles by a plurality of light sources, preferably three to five. For each direction of illumination, separate image data are recorded by time or by color division multiplex techniques. However, at this point, it should be remarked that the number of required light sources depends on the complexity of the particular object. In the case of simple geometries, one will do with less light sources than in the case of complex geometries.

As previously mentioned, a single camera is used for recording. In so doing, recordings successively made of the same object occur from a predetermined position. In this connection, it is quite possible that different recordings are made under differently illuminated conditions for purposes of successively detecting different regions of the object via its shadow cast. In any event, the camera is stationarily arranged, so that insofar an adequate protection of the camera is realizable even in a dirty surrounding or damaging atmosphere.

In this connection, it will be of further advantage, when the camera records the object from above, the front, or from other directions, always at the same angle with the object. As previously mentioned, the camera could be encased at least in the region of its lens, to be able to effectively avoid damage to the camera or its sensitive lens.

Basically, the casing of the camera could be closed, and would be opened—in the region of its lens—only for recording pictures. This would create an optical protection of the camera.

An essential component of an apparatus for operating the method of the invention is a computer, which is used on the one hand for controlling the illumination and camera, and the other hand for processing, or editing, and finally storing the obtained data. The computer may be a commercially available PC with the most up to date processor engineering and an adequate base memory.

Naturally, the meaning and purpose of the method according to the invention is less the mere detection of defects, but rather the making available of control data for the production process, such as, for example, core shooting. Thus, it would be possible to effectively avoid in the case of detecting a "defective part", that, for example, a defective core reaches assembly, and that by its presence the entire core packet qualifies as a "defective part." To this extent, it will be of special advantage, when the computer communicates with a stored program control (SPC), wherein process signals and result signals are exchanged between the computer and the stored program control. A process control may occur with obtained and processed data, as well as with edited data.

In a quite especially advantageous manner, a qualitative or quantitative image processing occurs on the recorded images or respective data. Basically in this instance, the recordings of the particular objects are compared with a reference image. This reference image is computed from a reference data record, which consists of n images of workpieces classified as "satisfactory." The reference image corresponds to the statistical mean value of the individual images of the data record. This procedure allows to lessen the influence of the process-inherent variation bandwidth of satisfactory parts in the computation of the reference image. At the same time, it is possible to use the extent of the variation bandwidth within the quality class to determine in a suitable manner the threshold values in the subsequent detection of defects for purposes of avoiding a too high probability of false alarms.

Finally, a variance comparison occurs. For purposes of this comparison, it would be possible to prepare a delta frame, which shows no structures in the ideal case, for example, which is entirely filled in black. In such a case, there would be a total match between the test image and the reference image.

Concretely, the image processing could comprise a coarse correlation, namely a rough comparison with the data of the reference image, or with limit values that are preferably predeterminable as gray-scale values. These limit values could be made variable, i.e., predetermined by the user. Depending on the object, it would furthermore be possible to record at least two images, which are added or subtracted from each other for further processing.

In a further advantageous manner, the image processing comprises an automatic position correction, which compensates, vis-a-vis the reference data, possible translational and rotational position inaccuracies of the object being actually examined. This allows to achieve a clear increase of the sensitivity of the system to the searched defects. The position correction may occur not only with reference to fixed marks on the workpiece itself, but also alone with reference to significant object structures by means of a correlation technique.

Furthermore, the image processing could also comprise a brightness adjustment for adapting the gray-scale values of the recording. This would take account of the situation that identical objects may reflect differently strong, which results in different measured values. In this process, system-immanent defects are also compensated.

As previously mentioned, the image processing could furthermore comprise a subtraction with filtering functions, if need arises. This subtraction is used for strengthening and highlighting the searched defects. The filtering functions are used for lessening interferences with obtained data, provided this is possible on the basis of the object. Finally, the image processing comprises a defect detection and edited or processed data in accordance with the foregoing description. Within the scope of such a defect detection, it will be of further advantage, when the detection sensitivity to a defect appearing on the object is freely definable with reference to a predeterminable threshold value. To this end, it is possible to predetermine a limit value for distinguishing between the defective and the satisfactory part.

In a further advantageous manner, the data of an image recording are reduced, in that one realizes a special RoI handling, namely that one continues to process only data of regions of interest (RoI). In this instance, other data are of no interest.

Concretely, predeterminable regions of the recorded image could be adapted for extraction or elimination. For the extraction and/or elimination, it would again be possible to predetermine threshold values or gray-scales values corresponding to the threshold values. In this process, the regions of interest can be easily marked for interactive processing via a monitor. Regions prone to defects or damage may be examined with very special attention. In this process, it is possible to reduce the data quantity as a whole. An individual parameterization of the individual regions of interest (RoI) leads to a further increase in the detection performance.

The apparatus of the present invention accomplishes the above-described object by the provision of an apparatus which is characterized in that for illuminating the object, at least two light sources are provided, which illuminate the object from different directions or angles, and a camera which is used for recording the object and the shadows formed on a base as a result of the illumination. For purposes of avoiding repetitions the description of the method according to the invention is herewith incorporated by reference.

There exist various possibilities of improving and further developing the teaching of the present invention in an advantageous manner. To this end, one may refer on the one hand to the dependent claims, as well as the subclaims, and on the other hand to the following description of an embodiment of the invention with reference to the drawing. In conjunction with the preferred embodiment of the invention with reference to the drawing, generally preferred improvements and further developments of the teaching are also described in greater detail. In the drawing:

DETAILED DESCRIPTION OF THE PREFERRED EMBODIMENTS

Figure 1:
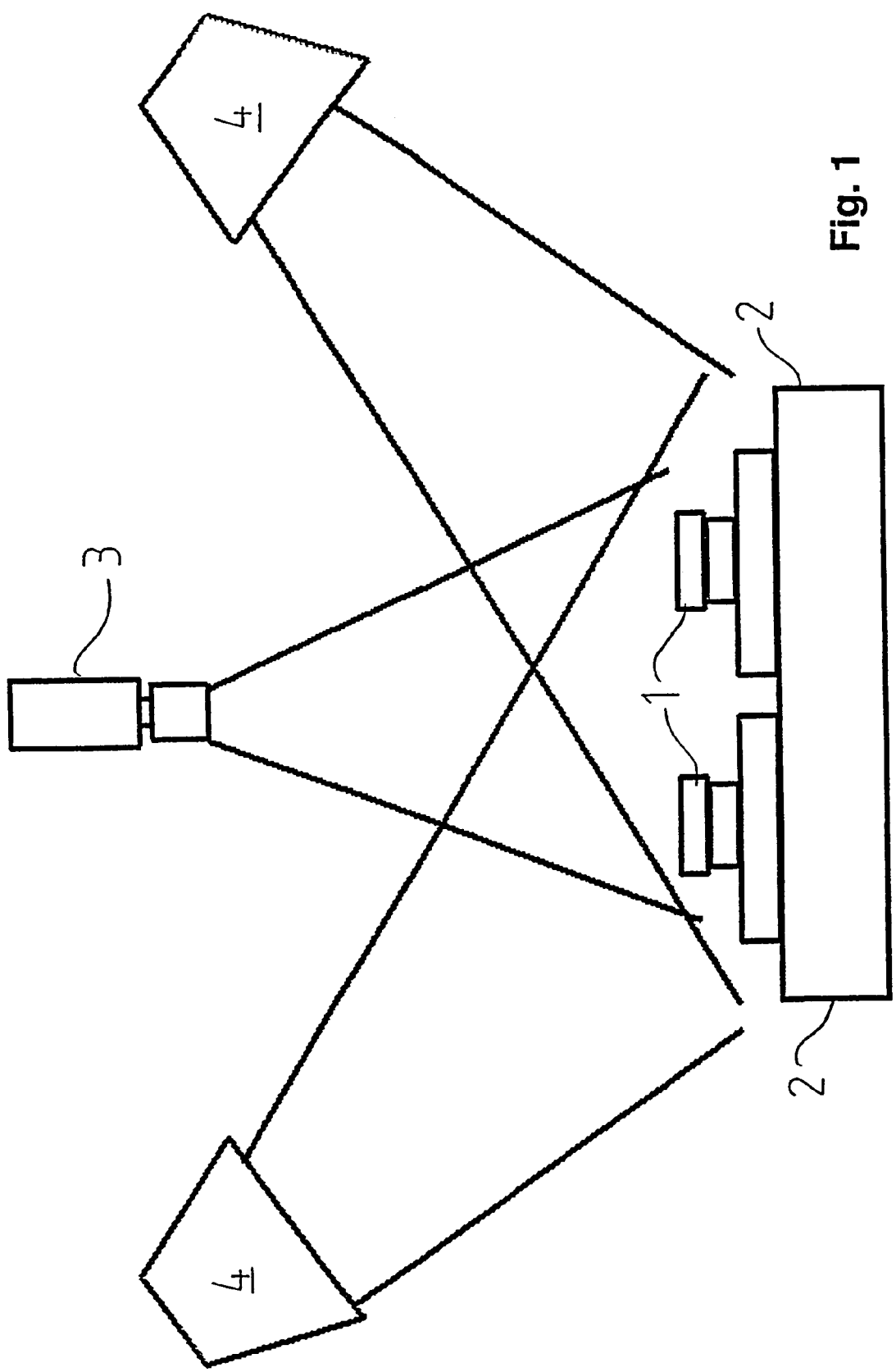
FIG. 1 is a schematic view of an apparatus according to the invention for object recognition, the apparatus being a device for detecting defects on shot cores.

The embodiment shown in FIG. 1 is an apparatus for detecting defects on shot cores 1. In the illustration, two cores 1 are placed on a base 2, which may be a pallet for transportation.

The apparatus comprises a camera 3 and two light sources 4, which illuminate cores 1 from different directions or angles, so that the camera 3 detects not only cores 1 in accordance with their contours, but also shadows caused by light sources 4.

Figure 2:
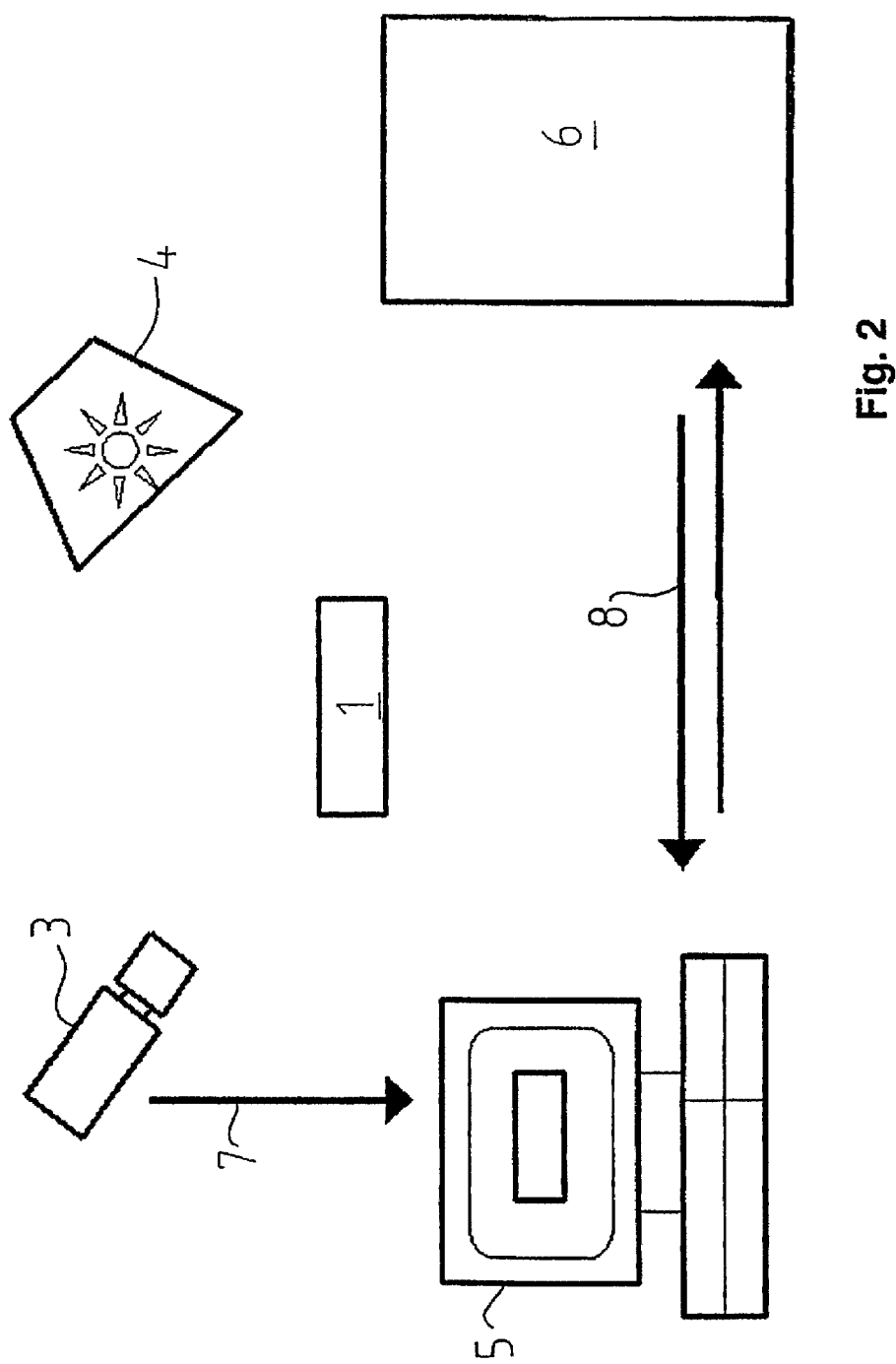
FIG. 2 is a schematic view of the mode of operation of the apparatus according to the invention.

As shown in FIG. 2, the camera 3 and light sources 4 are used for recording the images of core 1. In this connection, the camera 3 and likewise the light source 4 may be controlled via a processor. Specifically, in the illustrated embodiment, a PC 5 is provided, which receives images 7 that are taken by camera 3. The embodiment shown in FIG. 2 further includes a process control by means of a stored program control (SPC) 6. The stored program control (SPC) 6 communicates with PC 5, i.e., it transmits process signals and result signals 8.

In addition, it should be remarked that a more or less skillful arrangement of light source 4 results in a corresponding shadow of the object or core 1. The length of the shadow supplies data with respect to the z-axis. A concealed region on the object can thus be exactly projected therefrom, namely via its shadow. An examination of this region is possible, even when camera 3 is arranged in an actually unsuited position relative thereto. According to the projection, it is also possible to perform from the angle of view of the camera 3 an indirect inspection of certain regions of the object, which are not directly viewable by the camera 3.

On the monitor of PC 5 it is possible to realize different displays or ways of display. It would be possible to set up a plurality of user planes. For different core types, an automatic program change could be provided for purposes of minimizing changeover times in terms of electronic data processing.

Furthermore, it is possible that the PC 5 is connected online with a computer of the service or the manufacturing company of the entire system. In this respect, it would be possible to perform a remote maintenance.

Furthermore, it is essential that the previously described systematic procedure of the image analysis furnish a high flexibility of detection or evaluation. Any desired image manipulations as well as a reduction of the required data are possible.

Finally, it should be remarked that the stored program control (SPC) 6 could supply to PC 5 both a starting signal and signals relating to an automatic program change. From the PC, the status or data relating to measuring results are supplied to SPC 6. To this extent, it would be possible to use the SPC 6 for direct process controls within the scope of a primary production process.

Lastly, it should be expressly remarked that the above-described embodiment serves only for describing in greater detail the claimed teaching, without however limiting same to the embodiment.

What is claimed is:

1. A method of detecting defects on shot cores or core packets used in the foundry industry comprising the steps of
    illuminating each shot core or core packet by at least two light sources from different directions and so as to produce shadows which magnify an area of each shot core or core packet,
    recording by means of a camera each illuminated shot core or core packet and the magnifying shadows resulting from the illumination to thereby produce recorded data which comprise a recorded image, and
    processing the recorded data in a computer, and including processing the recorded image by comparing the recorded image with a record of reference data.

2. The method of claim 1, wherein the camera is arranged at a fixed location.

3. The method of claim 1, wherein the camera includes a lens and wherein the camera is encased at least in the region of the lens.

4. The method of claim 1, wherein the processing step includes exchanging signals between the computer and a stored program control.

5. The method of claim 1, comprising the further step of performing a qualitative or quantitative image evaluation on the recorded image.

6. The method of claim 1, wherein the comparing step includes a coarse correlation with the recorded data.

7. The method of claim 1, wherein the recording step includes recording at least two images which are processed in the processing step.

8. The method of claim 7, wherein the image processing step includes a position correction.

9. The method of claim 8, wherein the position correction includes recording reference marks.

10. The method of claim 9, wherein the reference marks are lines and/or dots on a base.

11. The method of claim 1, wherein the image processing step comprises a defect detection.

12. A method of detecting defects on shot cores or core packets used in the foundry industry comprising the steps of
illuminating each shot core or core packet by at least two light sources from different directions and so as to produce shadows which magnify an area of the core or core packet,
recording by means of a camera each illuminated shot core or core packet and the magnifying shadows resulting from the illumination to thereby produce recorded data which comprise a recorded image, and
processing the recorded data in a computer and including processing the recorded image by comparing the recorded image with a record of reference data, and
wherein the processing step further includes a brightness adjustment for adapting the gray-scale values of the image.

13. The method of claim 1, wherein the at least two light sources are operated in sequence.

14. The method of claim 1, wherein the at least two light sources are operated with color differentiation.

* * * * *